(12) United States Patent
Belhe et al.

(10) Patent No.: US 7,850,654 B2
(45) Date of Patent: Dec. 14, 2010

(54) DEVICE AND METHOD FOR POSITIONING A CLOSURE DEVICE

(75) Inventors: Kedar Ravindra Belhe, Minnetonka, MN (US); Andrew Thomas Forsberg, Minneapolis, MN (US)

(73) Assignee: St. Jude Medical Puerto Rico B.V., Amsterdam (NL)

( * ) Notice: Subject to any disclaimer, the term of this patent is extended or adjusted under 35 U.S.C. 154(b) by 1483 days.

(21) Appl. No.: 10/422,614

(22) Filed: Apr. 24, 2003

(65) Prior Publication Data

US 2004/0215232 A1    Oct. 28, 2004

(51) Int. Cl.
A61M 5/178    (2006.01)
A61B 17/08    (2006.01)
A61D 1/00    (2006.01)

(52) U.S. Cl. .................... 604/167.06; 604/166.01; 604/168.01; 606/213

(58) Field of Classification Search ............ 604/167.06; 606/153, 213; 600/504
See application file for complete search history.

(56) References Cited

U.S. PATENT DOCUMENTS

| | | | | |
|---|---|---|---|---|
| 3,459,189 A | * | 8/1969 | Alley et al. ............ | 604/166.01 |
| 4,202,332 A | * | 5/1980 | Tersteegen et al. ...... | 604/164.02 |
| 4,317,445 A | * | 3/1982 | Robinson ............... | 604/168.01 |
| 4,365,630 A | | 12/1982 | McFarlane | |
| RE31,873 E | * | 4/1985 | Howes ........................ | 600/487 |
| 5,030,207 A | * | 7/1991 | Mersch et al. ......... | 604/168.01 |
| 5,108,421 A | | 4/1992 | Fowler | |
| 5,163,904 A | * | 11/1992 | Lampropoulos et al. .................... | 604/100.02 |
| 5,192,300 A | | 3/1993 | Fowler | |
| 5,275,616 A | | 1/1994 | Fowler | |
| 5,306,254 A | * | 4/1994 | Nash et al. ............. | 604/168.01 |
| 5,478,352 A | | 12/1995 | Fowler | |
| 5,486,159 A | * | 1/1996 | Mahurkar .................. | 604/6.16 |
| 5,522,399 A | | 6/1996 | Wilk et al. | |
| 5,542,936 A | | 8/1996 | Razi | |
| 5,591,205 A | | 1/1997 | Fowler | |
| 5,601,602 A | | 2/1997 | Fowler | |
| 5,643,318 A | | 7/1997 | Tsukernik et al. | |
| 5,676,689 A | * | 10/1997 | Kensey et al. ............... | 606/213 |

(Continued)

FOREIGN PATENT DOCUMENTS

EP    1 262 149 A1    12/2002

(Continued)

OTHER PUBLICATIONS

Hales, Stephen. Encyclopaedia Britannica. 2007. Encyclopaedia Britannica Online. Oct. 30, 2007 <http://www.search.eb.com/eb/article-9038874>.*

(Continued)

Primary Examiner—Nicholas D Lucchesi
Assistant Examiner—Ian K Holloway
(74) Attorney, Agent, or Firm—Dorsey & Whitney LLP; Devan V. Padmanabhan (57) ABSTRACT

A vascular closure device including a sheath with one or more orifices therein to detect blood flow, indicating that the sheath has entered an artery and the relative position of the sheath within the artery. Thus, the sheath can be moved and positioned relative to the artery without having to completely extract the sheath from the artery after initial penetration.

19 Claims, 10 Drawing Sheets

U.S. PATENT DOCUMENTS

| | | | |
|---|---|---|---|
| 5,716,375 A | 2/1998 | Fowler | |
| 6,033,427 A * | 3/2000 | Lee | 606/213 |
| 6,302,898 B1 * | 10/2001 | Edwards et al. | 606/214 |
| 6,350,274 B1 * | 2/2002 | Li | 606/213 |
| 6,682,489 B2 | 1/2004 | Tenerz et al. | |
| 7,025,748 B2 * | 4/2006 | Ashby | 604/168.01 |
| 7,144,411 B2 * | 12/2006 | Ginn et al. | 606/213 |
| 7,201,725 B1 * | 4/2007 | Cragg et al. | 600/587 |
| 2004/0204654 A1 * | 10/2004 | Egnelov et al. | 600/504 |
| 2005/0004513 A1 * | 1/2005 | Beyerlein | 604/66 |

FOREIGN PATENT DOCUMENTS

| | | |
|---|---|---|
| WO | WO 02/28286 A1 | 4/2002 |

OTHER PUBLICATIONS

G. Dangas et al., Vascular Complications After Percutaneous Coronary Interventions Following Manual Compression Versus Arteriotomy Closure Devices, *Journal of the American College of Cardiology*, 2001 (38:3; pp. 638-641).

A. Denktas, et al., "Commentary—Angio-Seal Use in Overweight Patients: Is Angio-Seal Use Safe in Overweight Patients or is it Unsafe in Lower-Weight Patients?", *Journal of Invasive Cardiology*, 2001 (13:9; pp. 626-627).

K. Kahn, et al., "Safety of Suture-Medicated Closure Devices", *Catheterization and Cardiovascular Interventions*, 2002 (55:8-13).

Semler, "Efficacy of Invasive Vascular Closure Devices for Femoral Hemostasis", *American Journal of Cardiology*, 2001 (87:504).

Semler, "Femoral Hemostasis—Correspondenc", *Texas Heart Institute Journal*, 2001 (28,1:76).

"Complications Related to the Use of Vascular Hemostasis Devices", *Letter Published by FDA Center for Devices and Radiological Health*, Oct. 1999.

Morasch, Mark D., et al., "Perclose and 'Preclose' Devices for Endovascular Procedures: What Are The Real Advantages and Disadvantages", *28th Annual Montefiore Vascular & Endovascular Symposium*, New York, NY, Nov. 2001 (2pgs).

* cited by examiner

DEVICE AND METHOD FOR POSITIONING A CLOSURE DEVICE

BACKGROUND

The present invention relates to catheters and medical procedures involving catheters. More specifically, the present invention relates to wound closure devices, including vascular wound closure devices, and devices and methods for positioning wound closure devices, including relative to a blood vessel.

Various catheterization procedures require the piercing of a blood vessel, including arteries, or a body organ. Withdrawal of the catheter leaves a puncture wound that must be closed. For pierce or puncture wounds in blood vessels, traditional closure techniques involve withdrawal of the catheter and subsequent application of pressure to the area of the puncture to facilitate natural clotting. Such a technique is time consuming, and the time required and the results vary greatly from patient to patient.

The assignee of the present application owns patents and patent applications directed to vascular closure devices and their use. For example, U.S. Pat. Nos. 5,108,421, 5,192,300, 5,275,616, 5,478,352, 5,591,205, 6,601,602 and 5,716,375, all entitled "Insertion Assembly and Method of Inserting a Vessel Plug into the Body of a Patient," disclose closure devices and methods of using them.

U.S. Pat. No. 5,306,254, which issued Apr. 26, 1994 and is incorporated herein by reference in its entirety, describes a vascular closure device and method involving introducing a mechanical seal through a sheath. Generally, the disclosed closure device enables sandwiching an arteriotomy between a bio-absorbable anchor and a collagen sponge, both of which dissolve after time. This technique consistently, reliably, and bio-mechanically seals the puncture allowing for faster recovery as well as providing for a faster completion of the procedure.

During some catheterization procedures, a catheter procedure sheath is inserted into an artery and a given medical procedure, such as, for example, a cardiac catheterization, balloon angioplasty, angiographic dye injection or the like, is performed. Upon completion, a guidewire is inserted through the catheter sheath and into the artery. The procedure sheath is then removed, leaving the guidewire in place.

The assignee's vascular closure devices may then be used to seal the puncture. More specifically, an inserter or arteriotomy locator is introduced into a sheath of the vascular closure device. The guidewire is then fed through the arteriotomy locator. The combined arteriotomy locator and sheath are then advanced into the artery through the existing puncture, guided by the guidewire.

To determine the position of the sheath during insertion, a detection orifice is provided in the arteriotomy locator, just distal to the sheath tip. The orifice is in fluid communication with a proximal orifice (or other indicator) that is visible to the surgeon. Thus, the arteriotomy locator and sheath are advanced through the artery wall, until a "flashback" (e.g., blood flow) is detected in the proximal orifice indicating that the detection orifice is within the artery. It should be understood that the present invention need not be used exclusively on arteries; however, if it is being used on an artery, the blood flow may be pulsitile. When blood flow is detected, the sheath and arteriotomy locator are then retracted just until the flashback has ceased. This indicates that the detection orifice is aligned with the interior edge of the artery wall and the sheath has been retracted from the artery. As such, the arteriotomy locator and sheath are now in a known position relative to the artery. Both can be advanced a specific distance (e.g., 1-2 cm) and the surgeon is assured of proper placement of the arteriotomy locator and sheath relative to the artery. It is desirable to limit the advancement of the sheath so as to not pass the sheath too far into the artery. Some surgeons may repeat these steps (advancing and retracting) several time to obtain a comfort level with the position of the sheath.

Once properly positioned, the arteriotomy locator and guidewire are withdrawn through the sheath. An anchor device is inserted through the sheath and into the artery. The anchor is deployed so as to engage the tip of the sheath. That is, the tip of the sheath is specifically shaped and contoured to engage the anchor and cause it to move to a locking or engaging position wherein retraction through the sheath is precluded. The sheath is withdrawn exposing a coupling to the anchor that includes a suture, an advancer, and a collagen sponge. In short, the collagen sponge in pressed against the outer artery wall by repeated strokes of the advancer. This serves to compress the collagen sponge against the outer wall while cinching the anchor to the inner wall. The suture remains and holds these components in this configuration. The exposed portion of the suture is trimmed and the anchor, suture and collagen sponge dissolve within the body after a period of time (e.g., 60-90 days). In this manner, the arteriotomy is hemostatically sealed.

The vascular closure device described above is effective at rapidly sealing an arteriotomy. However, during the initial insertion of the arteriotomy locator and sheath, the retraction of the arteriotomy locator and the sheath requires the withdrawal of the sheath from the artery. That is, the position of the detection orifice is distal to the tip of the sheath; thus, when the detection orifice is aligned with the edge of the artery wall the sheath tip is necessarily withdrawn from said wall. Upon subsequent advancement, the sheath must re-penetrate the artery wall. Such advancement occurs at least once to properly position the sheath tip within the artery and may occur several times if the surgeon elects to reposition the device. While in most instances the advancement and retraction does not cause any difficulty, repeated penetrations could potentially adversely affect the vessel wall.

Thus, there exists a need to position a vascular wound closure device relative to a blood vessel without the sheath penetrating the vessel multiple times.

SUMMARY

In one embodiment, the present invention comprises a device for positioning a vascular wound closure device comprising a sheath having a distal end and a proximal end, a first detection orifice located near the distal end, and a first locator orifice near the proximal end, wherein the first detection orifice is in fluid communication with the first locator orifice such that when the first detection orifice is disposed within a blood vessel and exposed to blood flow, such blood flow is indicated at the first locator orifice. The invention encompasses a method of positioning a vascular wound closure device in a vascular closure procedure, wherein, in one embodiment, the method comprises inserting a distal end of a sheath into a blood vessel, advancing the sheath until blood flow is detected at an orifice disposed on the sheath, retracting the sheath until the blood flow ceases without completely withdrawing the sheath from the blood vessel, and determining that the orifice is positioned adjacent an edge of the vessel wall. The method further comprises advancing the sheath forward from the determined edge a predetermined distance.

The present invention, in one embodiment, is a vascular closure device comprising a sheath having a distal end and a proximal end and a first detection orifice located in the sheath near the distal end. The device also includes a first locator orifice disposed in the sheath near the proximal end, wherein the first detection orifice is in fluid communication with the first locator orifice such that when the first detection orifice is disposed within a blood vessel and exposed to blood flow, such blood flow is indicated at the first locator orifice.

The present invention also includes a method of using a catheter device in a vascular closure procedure, wherein, in one embodiment, the method comprises inserting a distal end of a sheath into blood vessel wall. The method also includes advancing the sheath through the blood vessel until blood flow is detected at an orifice disposed on the sheath and retracting the sheath until the blood flow ceases without completely withdrawing the sheath from the blood vessel and determining that the orifice is positioned adjacent an edge of the vessel wall. The method further includes advancing the sheath forward from the determined edge a predetermined distance.

The present invention also includes another method of using a catheter device in a vascular closure procedure. The method includes inserting a distal end of a sheath into the wall of a blood vessel, for example an artery, until blood flow is detected at a first orifice disposed on the sheath near the distal end indicating that the first orifice has entered the artery and advancing the sheath a predetermined distance into the artery. The method also includes stopping advancement if blood flow is detected at a second orifice disposed on the sheath at a further distance from the distal end than the first orifice is disposed.

In another embodiment, the present invention is a vascular wound closure device that includes a sheath for penetrating an artery, the sheath having a distal end and a proximal end. The device includes a first detection orifice disposed on the sheath, a second detection orifice disposed on the sheath further from the distal end that then first detection orifice and a first indicator in fluid communication with the first detection orifice via a first fluid passageway, the first indicator disposed on the sheath proximate the proximal end, wherein the first indicator indicates when the first detection orifice is exposed to blood flow. The device includes a second indicator in fluid communication with the second detection orifice via a second fluid passageway, the second indicator disposed on the sheath proximate the proximal end, wherein the second indicator indicates when the second detection orifice is exposed to blood flow.

While multiple embodiments are disclosed, other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

In the present invention, specific reference is made to exemplary embodiments of a catheter sheath and a vascular closure device and method. However, vascular closure devices and methods can take many forms and may be used in various catheterization, laproscopic, and minimally invasive procedures, and the position detecting features and steps of the present invention are intended to be applicable as suitable to any form of vascular closure device and method.

Figures 1A, 1B:
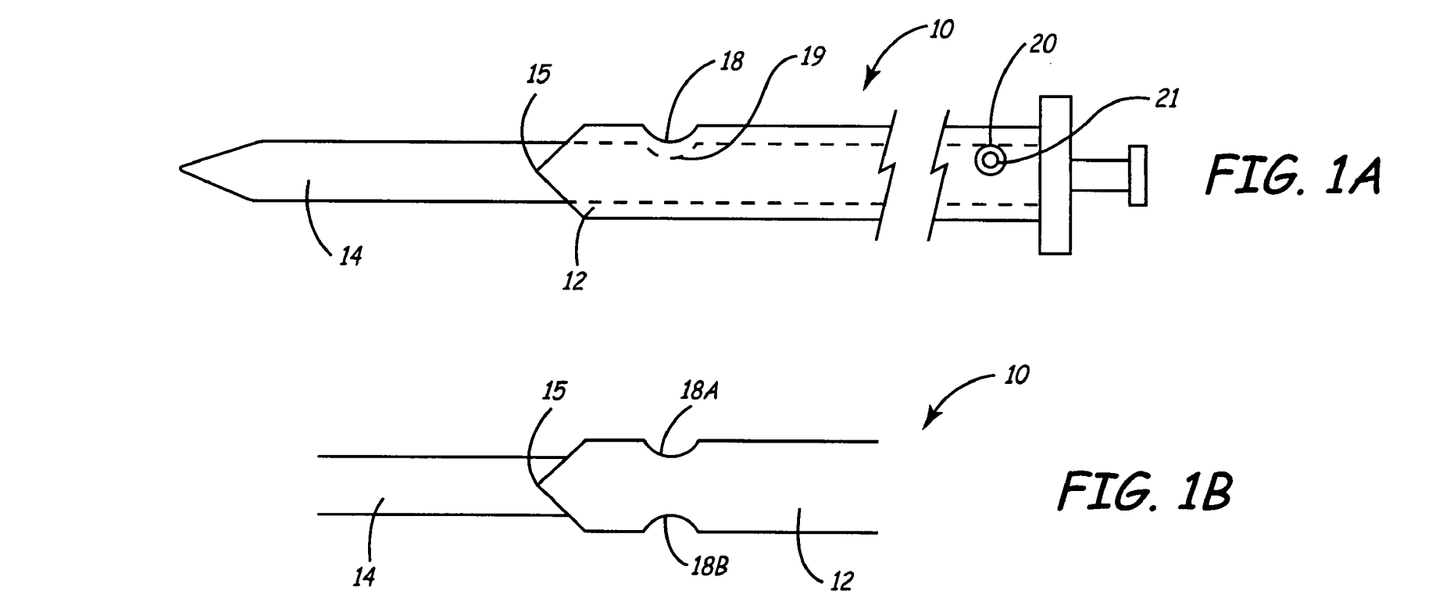
FIG. 1A is a side schematic view of a catheter device having a detection orifice disposed on a sheath.
FIG. 1B is a side schematic view illustrating two detection orifices disposed on the sheath.

FIG. 1A is a side view of a vascular closure device 10 that includes a sheath 12 and a arteriotomy locator 14 that is receivable within the sheath 12. The arteriotomy locator 14 is positionable over and guidable by a guide wire 16. It should be appreciated that the various components (e.g., the arteriotomy locator 14, guide wire 16) may be inserted into and removed from the sheath 12 before or after the sheath 12 has been passed through a wall of blood vessel. In other words, the sheath 12 provides a known access point once so inserted. The various components are made from any suitable material such as metal or medical grade plastic.

In one embodiment, the sheath 12 includes a detection orifice 18 located near a distal end of the sheath 12. The detection orifice 18 is in fluid communication with a locator orifice 20 that is located near a proximal end of the sheath 10 (or any suitable portion of the device 10), so that the locator orifice 20 is visible to a surgeon even when the sheath 12 is inserted through the wall of a blood vessel. The locator orifice 20 is an indicator that may take any configuration suitable to provide a visual, audible, and/or tactile indication of blood flow.

Fluid communication between the detection orifice 18 and the locator orifice 20 may be achieved in a number of ways. In one embodiment, the arteriotomy locator 14 includes a hollow passageway and a arteriotomy locator orifice 19. When properly positioned within the sheath 12, the arteriotomy locator orifice 19 aligns with the detection orifice 18. Similarly, the arteriotomy locator 14 includes an exit orifice 21 that aligns with locator orifice 20. Alternatively, the proximal end of arteriotomy locator 14 could be exposed and exit orifice 21 could function as the indicator (e.g., functionally replacing locator orifice 20). In another embodiment, a separate, dedicated lumen is provided within the sheath 12 between the two orifices 18, 20. In another embodiment, no such lumen is provided. Rather, the presence of the arteriotomy locator 14 within the hollow sheath 12 forms a fluid passageway between the detection orifice 18 and the locator orifice 20. In some embodiments, a gap between the interior cavity of the sheath 12 and the arteriotomy locator 14 forms the fluid passageway. It may be formed in other suitable ways, too. For example, the outer surface of the arteriotomy locator 14 or the inside surface of the sheath 12 may be provided with grooves or channels.

Figure 1C:
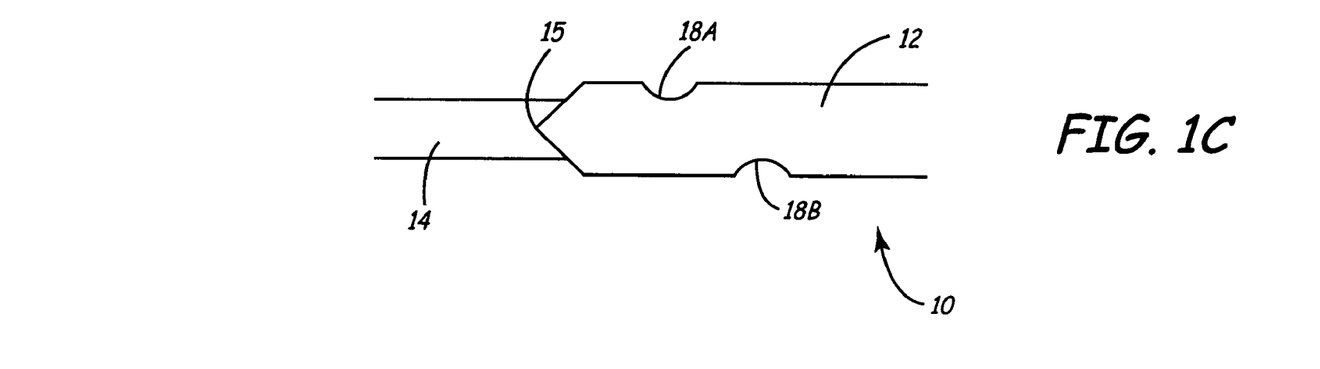
FIG. 1C is a side schematic view illustrating two, linearly offset orifices disposed on the sheath.

FIGS. 1B and 1C illustrate variations of the device 10, wherein two detection orifices 18A and 18B are provided and both are in fluid communication with the locator orifice 20. As will be explained more fully below, blood flow is observed through the locator orifice 20 to indicate proper positioning. Thus, by providing two (or more) detection orifices 18A, 18B, a larger volume of blood flow may be achieved to provide a greater indication. In FIG. 1B, the two orifices 18A, 18B are provided adjacent to one another. In FIG. 1C, the two orifices 18A, 18B are axially offset from one another. As the sheath 12 is generally inserted into the artery (or other blood vessel) at a non-perpendicular angle, this offset (indicated generally by the hatched line) will generally be positioned parallel to a main axis of the artery wall. Thus, both detection orifices 18A, 18B will be exposed to the same flow rates at the same time as the sheath 12 is moved and positioned through and within the artery.

Figure 2A:
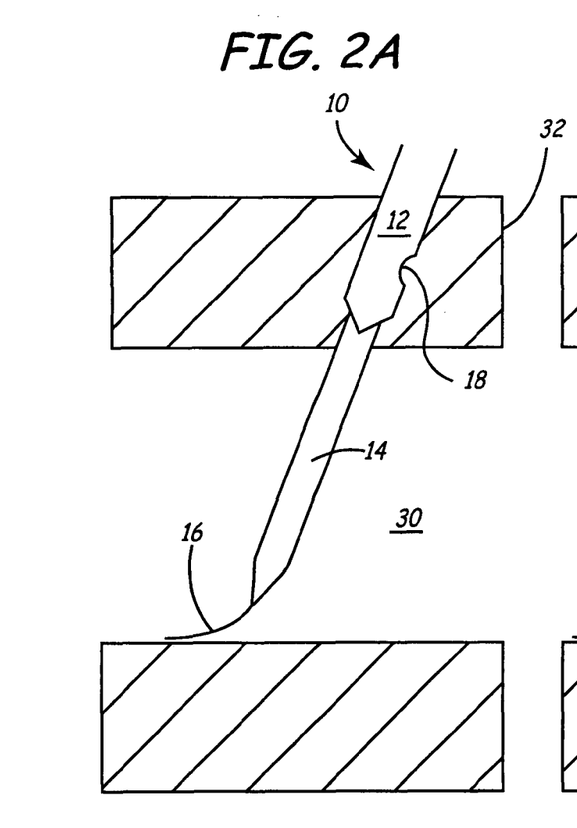
FIGS. 2A-2E schematically illustrate the sheath of FIG. 1 puncturing and entering an artery.
Figure 2B:
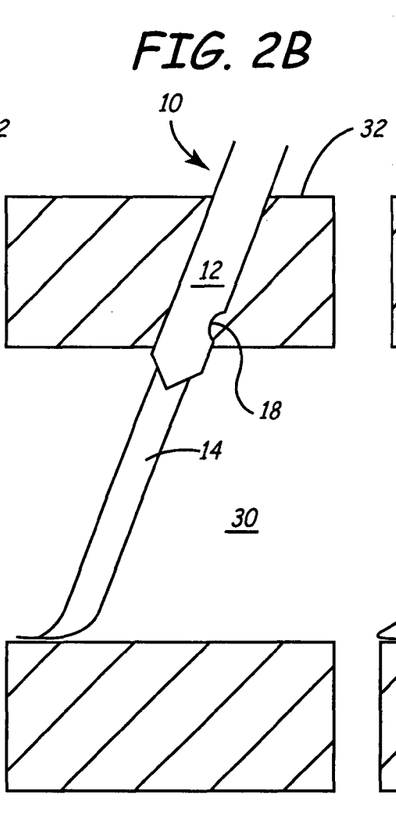
Figure 2C:
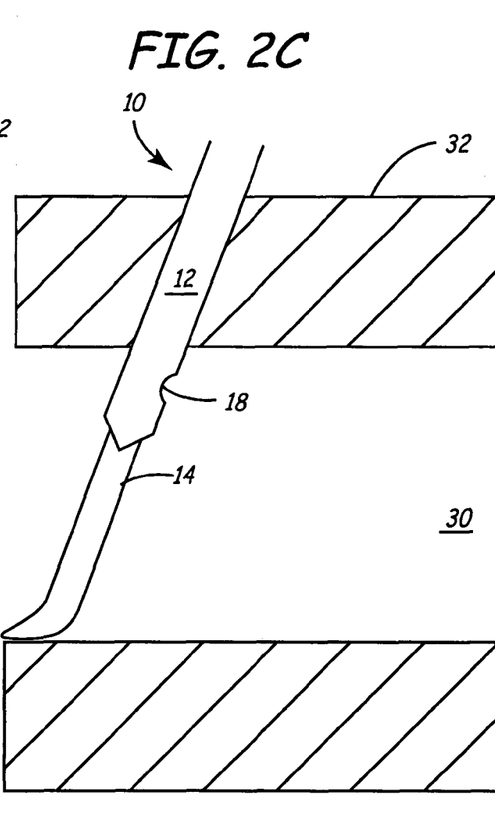

FIGS. 2A-2E schematically illustrate the deployment of the device 10 into an artery 30 through an artery wall 32, while using the present invention to properly position the device. In FIG. 2A, the sheath 12 partially pierces the artery wall 32. The arteriotomy locator 14 and the guidewire 16 are passed through the sheath and into the artery 30. As the device 10 is advanced in FIG. 2B, the distal end of the sheath 12 passes through the artery wall 32 and enters the artery 30. At this point, the detection orifice 18 is still occluded by the artery wall 32, thus no blood flow is detected at the locator orifice 20. The operator knows to further advance the device 10, as illustrated in FIG. 2C. As indicated, the detection orifice 18 is within the artery 30 and exposed to blood flow. Blood is delivered from the detection orifice 18 to the locator orifice 20 (or otherwise indicated). Thus, the operator now knows that the distal end 15 of the sheath and at least a portion of the detection orifice 18 is within the artery.

Once blood flow is detected, the operator knows that the sheath is properly positioned. That is, the tip or distal end 15 is just inside the artery 32 and the device is ready for anchor deployment. This is advantageous in that the device 10 is properly positioned with only one advancing and one retracting stroke, without removing the sheath 12 completely from the artery wall 32. That is, because the detection orifice 18 is positioned on the sheath 12, the retraction of the device 10 to find the edge of the artery wall 32 does not require the sheath 12 to be withdrawn from the wall 32. The space between the detection orifice 18 and the distal end 15 is such that locating the edge of the artery wall in the above manner, positions the distal end 15. Of course, a given operator may advance or retract the sheath 12 multiple times based upon a familiarity with previous devices (that required such actions) or to simply gain a comfort level with the positioning. The present invention is advantageous in this regard because such repetitive strokes still do not withdraw the sheath 12 from the artery wall 32. Thus, even though they are ultimately unnecessary, they are generally harmless.

Figure 2D:
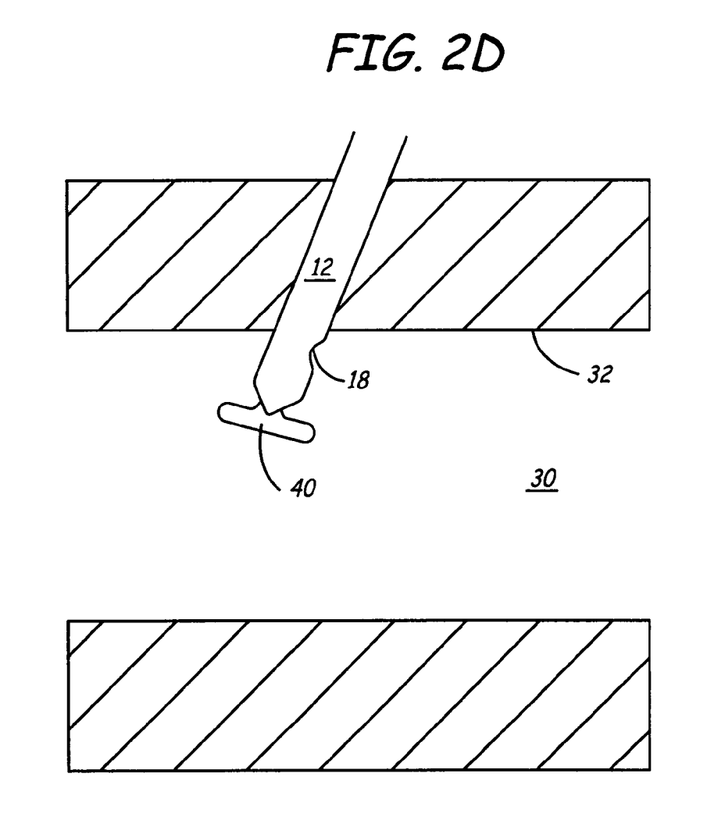
Figure 2E:
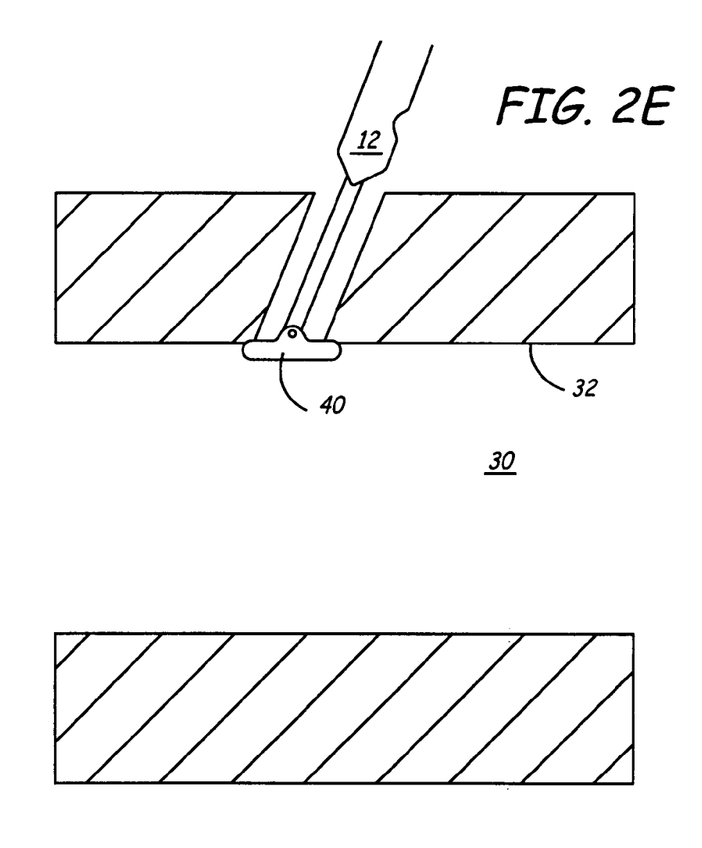

FIGS. 2D-2E, generally illustrate the deployment of an anchor 40. The anchor 40 is passed through the sheath 12 and into the artery. The sheath 12 is subsequently extracted and the anchor 40 is used as one half of a sealing device (within the artery) to seal the puncture.

Figure 3:
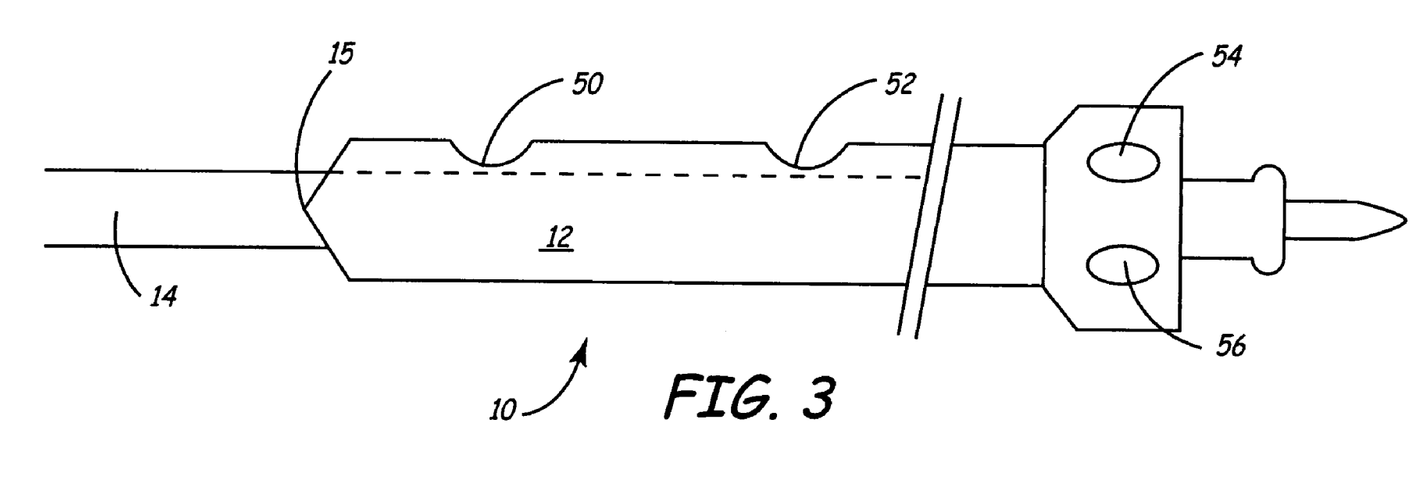
FIG. 3 is a side schematic view of a sheath having two detection orifices.

FIG. 3 illustrates another embodiment of the device 10 that includes a first detection orifice 50 and a second detection orifice 52. The first and second detection orifices 50, 52 are in fluid communication with a first locator indicator 54 and a second locator indicator 56 respectively. Once again, blood flow is detected at the appropriate indicator 54, 56 and blood is allowed to enter the appropriate orifice 50, 52.

In order to differentiate between the first orifice 50 and the second orifice 52, there are separate paths of fluid communication between the respective orifice 50, 52 and the indicator 54, 56. This can be accomplished with a separate lumen provided within the sheath 12 for each flow path. Alternatively, one such flow path could be the open interior or the sheath 12 as limited by the presence of the arteriotomy locator 14. One flow path could be the hollow interior of the arteriotomy locator 14, as described above. Thus, as blood flow is achieved through first detection orifice 50, such flow is indicated at the first locator indicator 54. Similarly, as blood flow is achieved through second detection orifice 52, such flow is indicated at second locator indicator 56. Thus, the first and second detection orifices 50, 52 act as position identifiers.

The orifices 50, 52 are selectively positioned on the sheath 12 to indicate a selected position within the artery 30. That is, the first detection orifice 50 is located near the distal end 15 of the sheath 12. Thus, as described above the first detection orifice indicates successful entry into the artery 30, beyond the artery wall 32. Continued advancement of the device 10 beyond this initial indication places the sheath 12 further into the artery. Blood flow through second detection orifice 52 and indicated by second locator indicator 56 indicates that the sheath 12 has advanced into the artery sufficiently far to allow second detection orifice 52 to be in fluid communication with the blood flow of the artery 30.

In one embodiment, the second orifice 52 is positioned so that if blood flow is detected, this indicates the sheath has been advanced "too far" and should be slightly retracted or at least not advanced farther. Alternatively, the second orifice 52 could be positioned so that once blood flow is detected, the operator knows the sheath is properly positioned. In either case, the recurrent advancing and retracting with previous embodiments may be avoided. That is, the sheath 12 can normally be inserted in a single advancing action, with at most, a slight retraction if a "too far" condition is reached. Alternatively, such an embodiment could be used as previously described with advancing and retracting strokes. The second indicator would simply provide an additional safety function of alerting the surgeon that the device 10 has been inserted too far.

Figure 4:
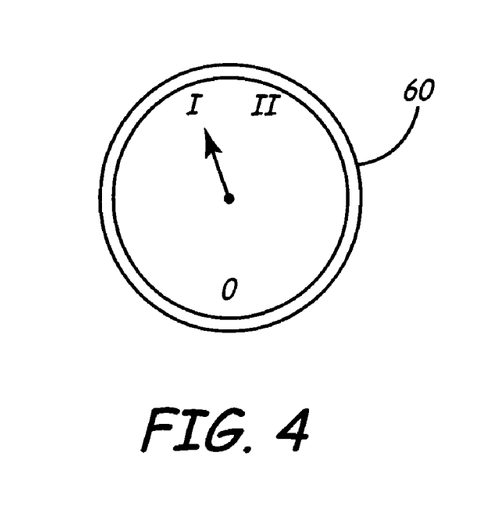
FIG. 4 is a schematic view of a dial display.
Figure 5:
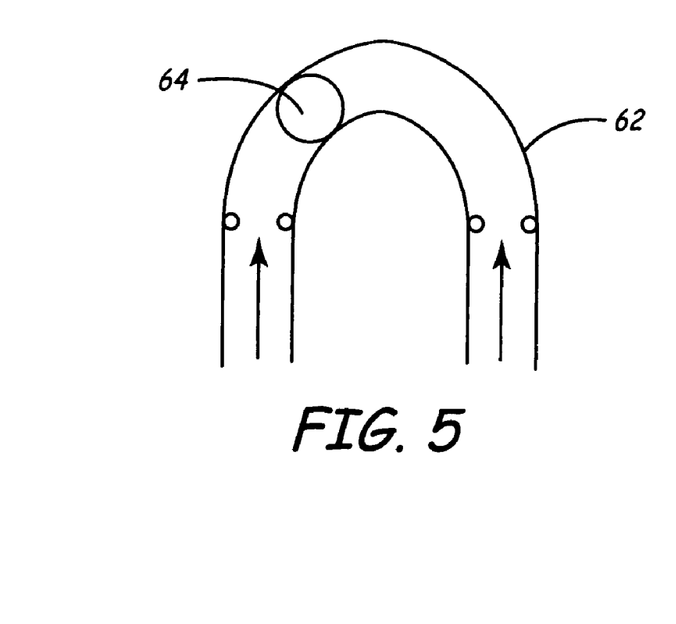
FIG. 5 is a schematic view of an indicator.

FIGS. 4 and 5 illustrate various indicators 60, 62 that can be provided as locator indicators 54, 56. In its simplest form, locator indicator 54, 56 is simply an opening through which blood flow occurs and is viewed or otherwise sensed. The locator indicator 54, 56 could be open to the environment or shielded by a viewing port. FIG. 4 illustrates dial-type display device 60 that indicates the absence of blood flow; blood flow at the first orifice 50 (I); or blood flow at the second orifice 52 (II). FIG. 5 illustrates a simple fluid communication path 62 interconnecting the two orifices 50, 52. The direction of the blood flow will move the indicator ball 64 to an appropriate point to indicate which orifice 50, 52 is within the artery 30.

Figure 6:
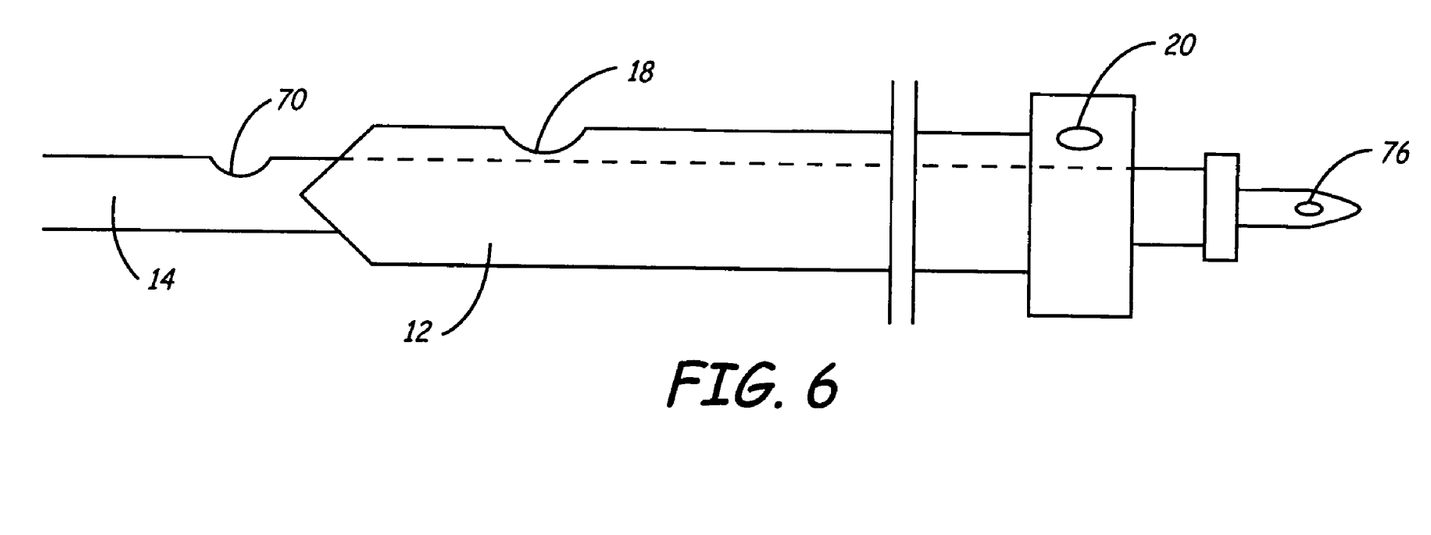
FIG. 6 is a side, partially sectional view of a catheter having an orifice in a sheath and an orifice in a arteriotomy locator.

FIG. 6 illustrates another embodiment wherein a arteriotomy locator orifice 70 is provided in the arteriotomy locator 14. The arteriotomy locator orifice 70 is in fluid communication with a arteriotomy locator indicator 76 disposed at a proximal end of the device 10. Similarly, a sheath orifice 18 is provided in the sheath 12 and functions in the same manner as previously described in conjunction with a sheath indicator 20. In this embodiment, blood flow initially indicated by the arteriotomy locator orifice 70 indicates that the distal end 15 of the sheath 12 is proximate the artery wall 32. Blood flow indicated at the sheath orifice 18 will indicate the location of the sheath orifice 18 relative to the artery wall 32. That is, depending on where the sheath orifice is positioned relative to the distal end 15, the detected blood flow could indicate different parameters. For example, when placed near the distal end 15, such blood flow could indicate the proper positioning of the sheath. If the sheath orifice 18 is positioned further away from the distal end 15, blood flow could indicate a "too far" positioning of the sheath 12. In either case, it is unnecessary to withdraw the sheath 12 from the artery wall during initial positioning and, thus, repetitive entry of the sheath 12 through the artery wall 32 is avoided.

Figure 7:
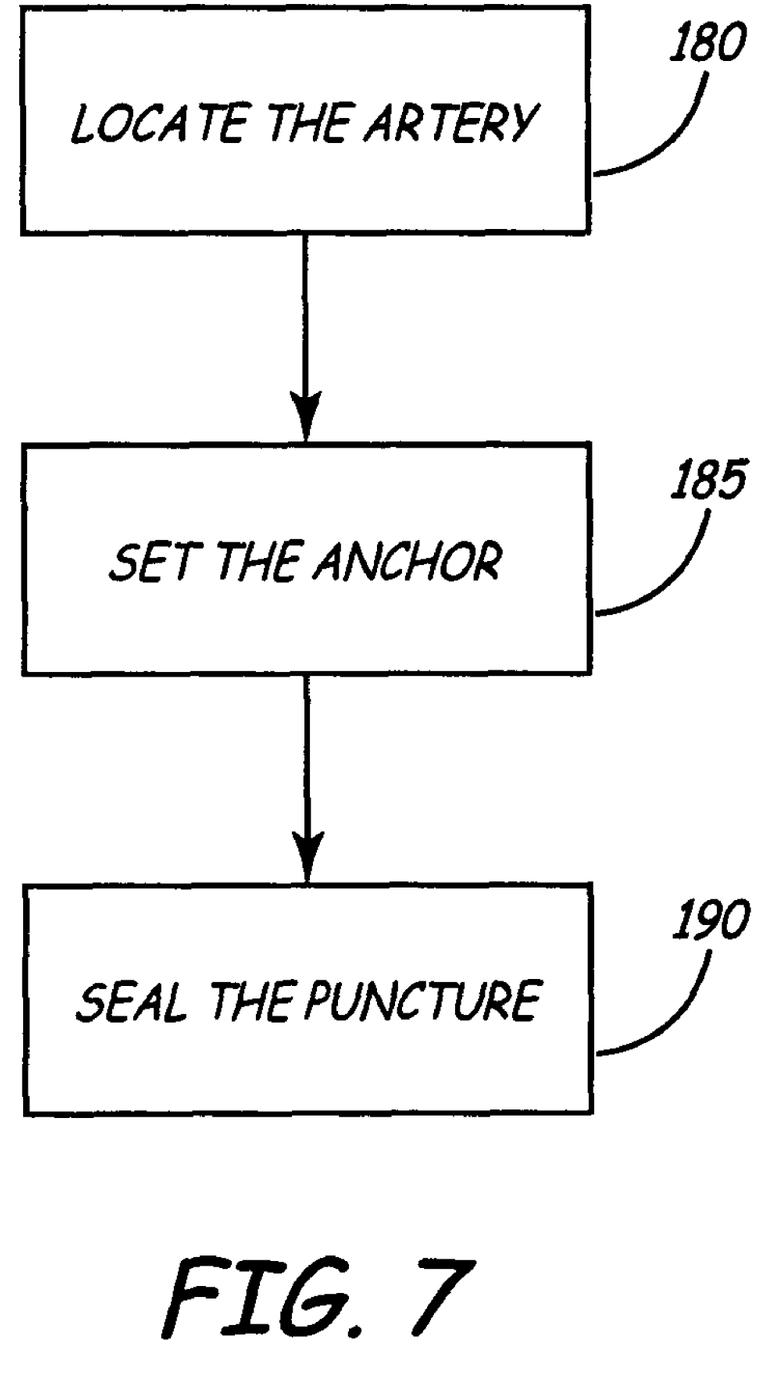
FIG. 7 is a flowchart illustrating the steps of scaling a puncture.

Referring to FIG. 7, in one embodiment an insertion procedure utilizing the device 10 comprises three steps: locate the blood vessel, in this instance an artery (180), set the anchor (185), and seal the puncture (190). Before beginning the procedure, the surgeon may conduct a fluoroscopic assessment of the arteriotomy region, to confirm the correct placement of the procedure sheath that is already in place, for example, in the common femoral artery.

Figure 8:
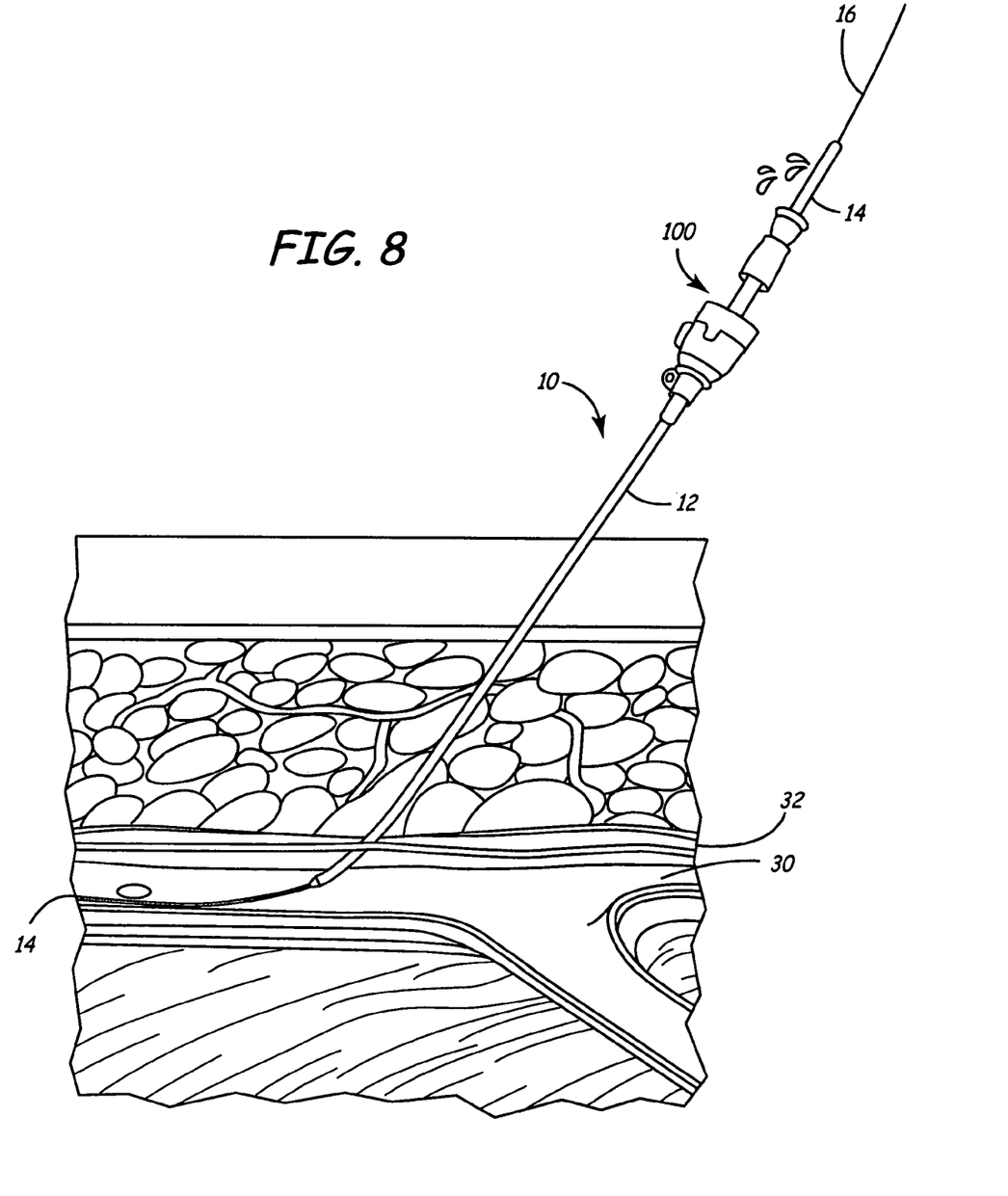
FIG. 8 is a side, sectional view of an insertion sheath and arteriotomy locator in an artery.
Figure 9:
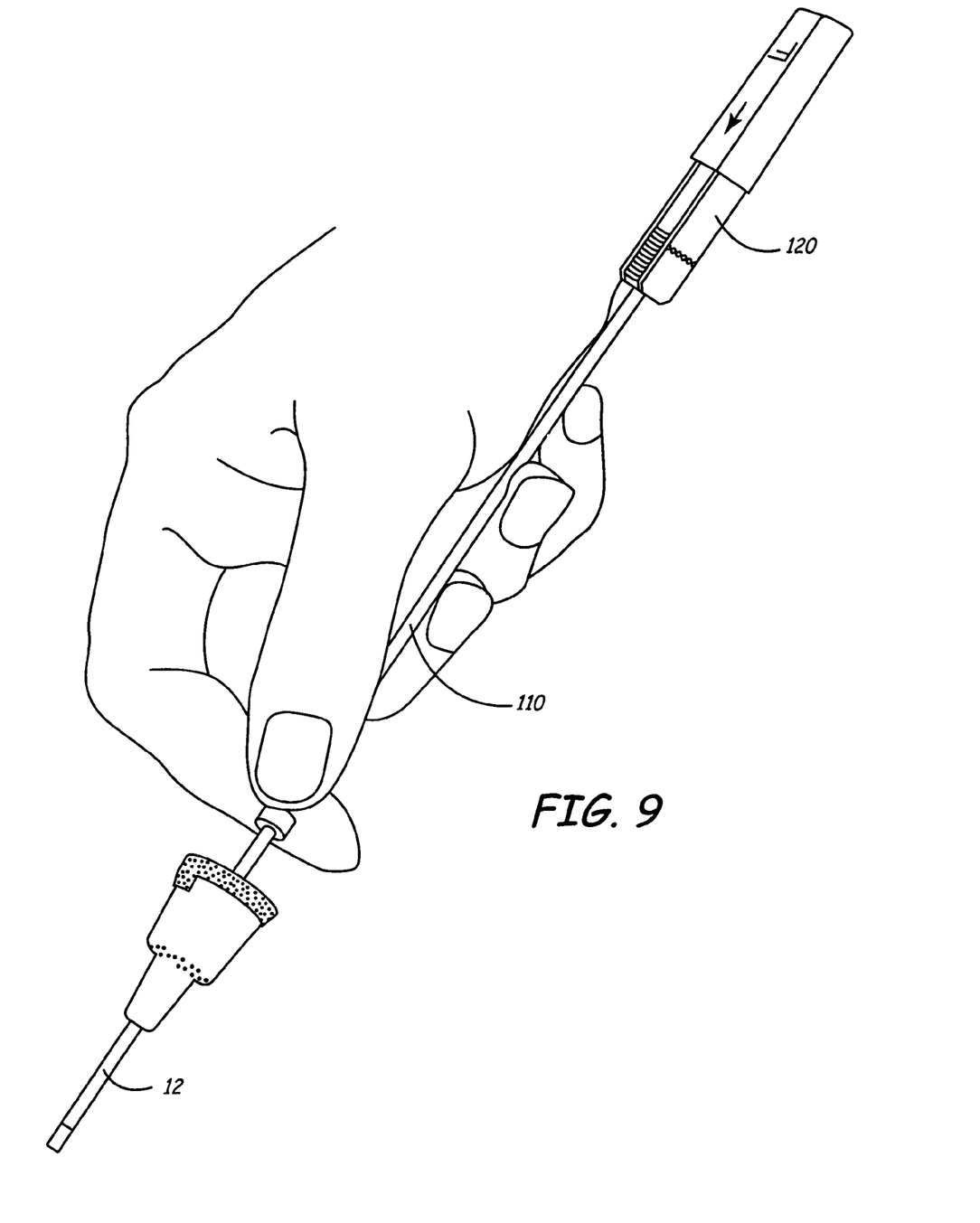
FIG. 9 is an illustration of an anchor device being inserted through an insertion sheath.
Figure 10:
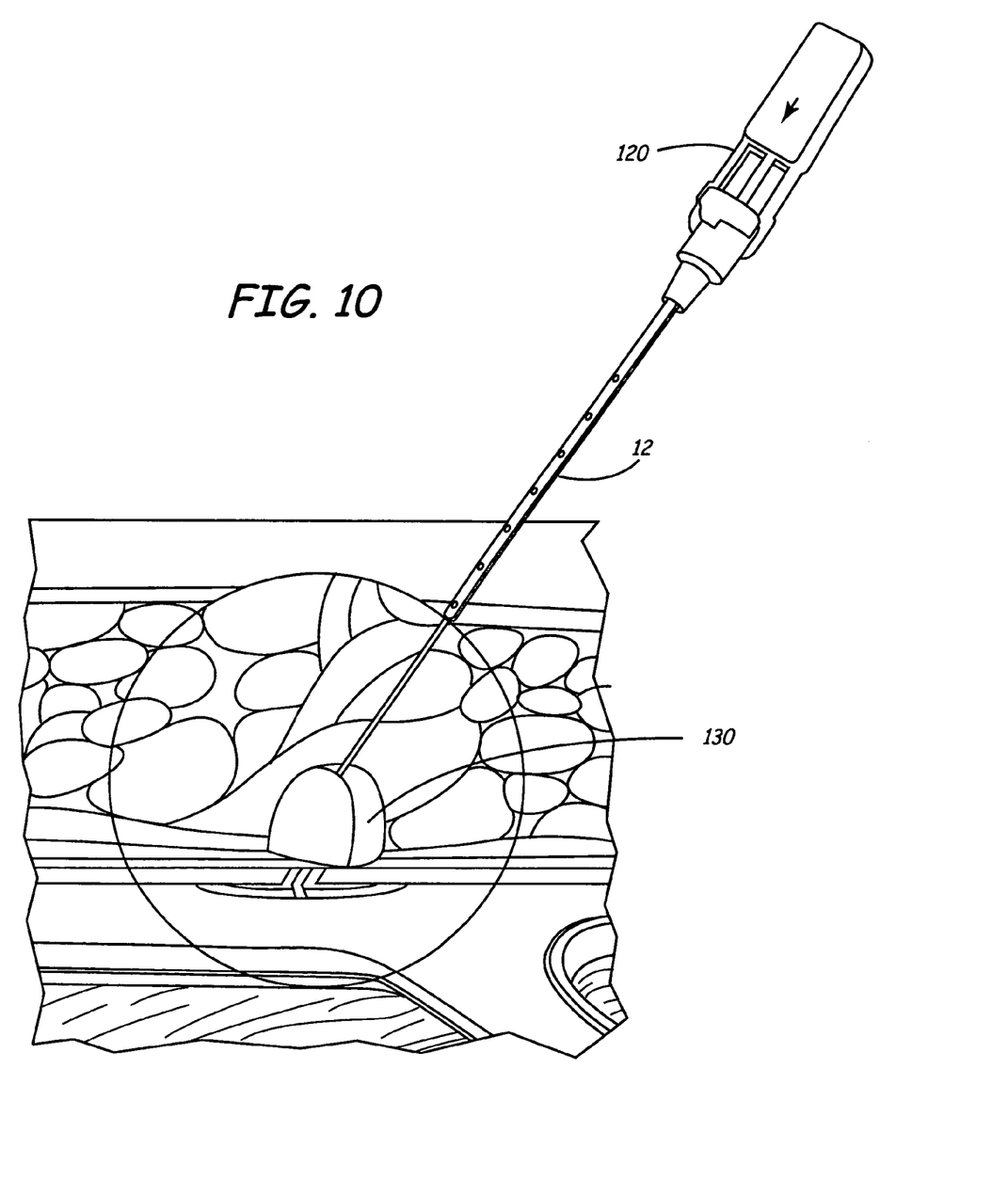
FIG. 10 is a side, sectional partially enlarged view of a set anchor.
Figure 11:
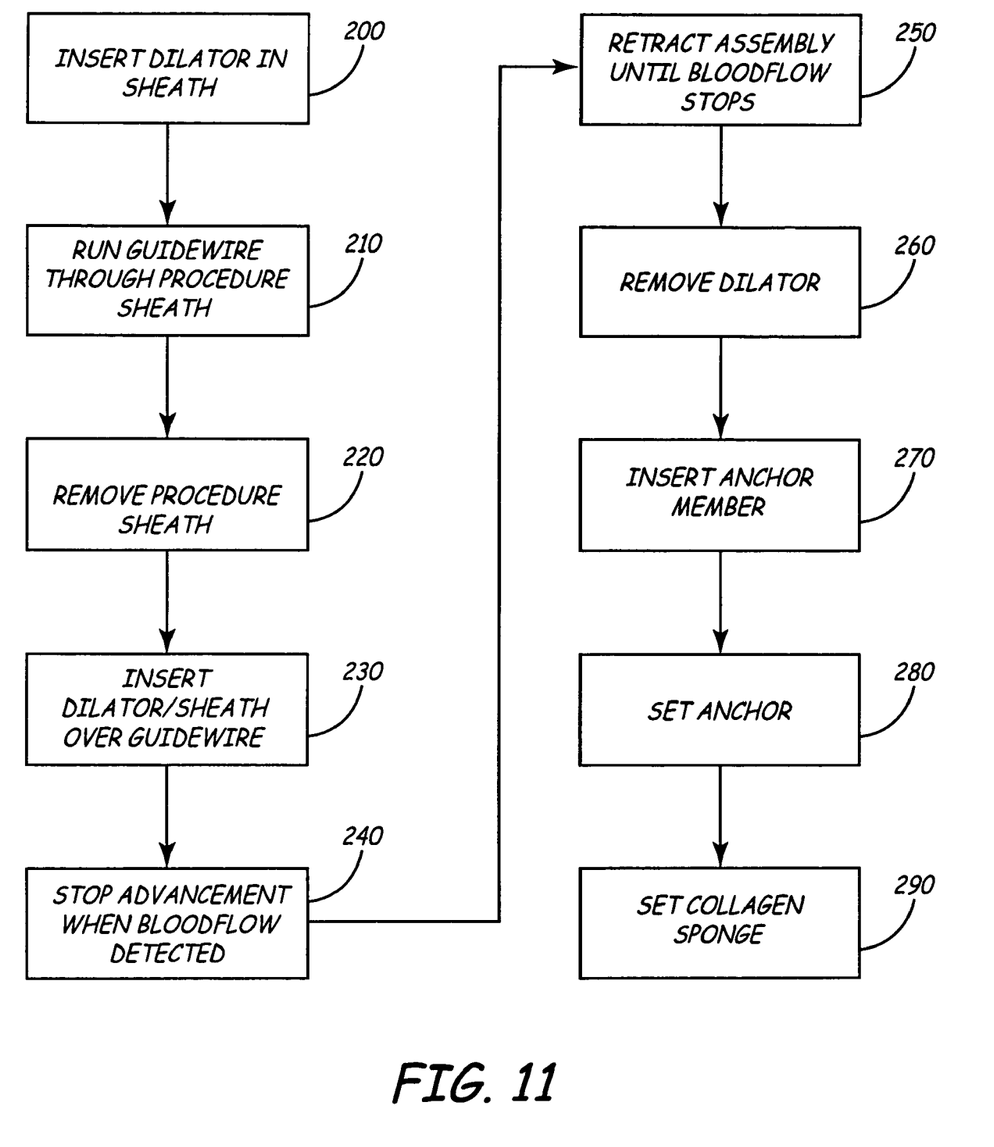
FIG. 11 is a flowchart illustrating the steps of inserting and setting the anchor.

The procedure will be described in reference to the flowchart of FIG. 11 as well as the illustrations presented in FIGS. 8-10. To begin the surgeon inserts and snaps (200) the arteriotomy locator 14 into the insertion sheath 12. The locking interaction between the sheath 12 and the arteriotomy locator 14 at a locking head 100 assures that the appropriate detection orifices are aligned. Next, the guide wire 16 is inserted (210) into the existing procedure sheath. The procedure sheath is removed over the guide wire 16. The locator insertion sheath 12 and arteriotomy locator 14 are inserted (230) over the guide wire 16.

The assembly is advanced through the puncture track and into the artery 30. When the tip 15 of the insertion sheath 12 enters the artery 30, blood will begin to flow from the proximal locator orifice 20 (240). The assembly is then backed out slowly until the blood flow stops (250), indicating that the detection orifice 18 has been occluded by the artery wall 32. The device 10 is now properly positioned. Earlier devices required subsequent advancement from this position. Thus, at least at first, subsequent advancement may be performed as a matter of habit for some surgeons. This will simply further advance the sheath 12 further into the artery. While unnecessary, this action is generally not harmful.

Once positioned, the proximal end of the arteriotomy locator 14 is bent down slightly, to unlock it from the insertion sheath. The arteriotomy locator 14 and guide wire 16 are removed (240) from the sheath 12. The anchor materials (110) are then advanced (270) into the sheath 12 as shown in FIG. 9. A secure cap 120 will only allow the device sleeve and sheath cap to fit together in the correct position. While holding the sheath hub steady within the artery, the secure cap is grasped and slowly pulled back until resistance is felt, indicating the anchor is now positioned against (280) the distal end 15 of the insertion sheath 12.

The device-sheath assembly is slowly withdrawn along the angle of the puncture track to position the anchor 40 against the artery wall 32. As the sheath 12 clears the skin, a tamper tube and suture will appear. The tamper tube is advanced to move (290) a collagen sponge 130 down the tissue track. The suture is retained within the cap 120 and appears as the sheath 12 is withdrawn. Tension is maintained on suture and the tamper tube is advanced along the puncture track to help form the collagen anchor seal at the arteriotomy. The seal is complete when resistance is felt and the tamping marker is revealed on the suture, above the tamping tube. This confirms that the self-tightening suture has secured the collagen sponge at the arteriotomy as illustrated in FIG. 10.

The procedure is completed by cutting the suture and removing the tamper tube. The remaining suture is pulled upwards and cut below skin level. The anchor, collagen sponge, and suture will be naturally absorbed by the body within sixty to ninety days.

The present invention is useful for any type of catheter that is placed within an artery or similar structure. In one context, the present invention is used with an artery puncture sealing apparatus, however, such use is merely meant to be exemplary and not limiting.

Although the present invention has been described with reference to preferred embodiments, persons skilled in the art will recognize that changes may be made in form and detail without departing from the spirit and scope of the invention.

We claim:

1. A device for positioning a vascular wound closure device comprising:
    a sheath having a distal end and a proximal end, a sealing device being insertable through the sheath;
    a first detection orifice in the sheath near the distal end;
    a second detection orifice in the sheath near the distal end;
    a first locator orifice in the sheath near the proximal end, and
    a second locator orifice in the sheath near the proximal end,
    wherein the first detection orifice is in fluid communication with the first locator orifice such that when the first detection orifice is disposed within the blood vessel and exposed to blood flow, such blood flow is indicated at the first locator orifice; and
    wherein the second detection orifice is in fluid communication with the second locator orifice such that when the second detection orifice is disposed within the blood vessel and exposed to blood flow, such blood flow is indicated at the second locator orifice.

2. The device of claim 1, wherein the second detection orifice is in fluid communication with the locator orifice.

3. The device of claim 1, wherein the first detection orifice and the second detection orifice are linearly aligned about a circumference of the sheath.

4. The device of claim 1, wherein the first detection orifice and the second detection orifice are linearly offset with respect to one another along an axis of the sheath so that upon non-perpendicular entry into the blood vessel, the first detection orifice and the second detection orifice are generally equidistant from a wall of the blood vessel.

5. The device of claim 1, wherein a fluid communication path from the first detection orifice to the first locator orifice is isolated from a second fluid communication path from the second detection orifice to the second locator orifice.

6. The device of claim 1, wherein the position of the first detection orifice is such that blood flow indicates a proper positioning of the sheath within the blood vessel and the position of the second detection orifice is such that blood flow indicates that the sheath has penetrated the blood vessel too far.

7. The device of claim 1, wherein the first locator orifice is an open outlet enabling passage of fluid from the device.

8. The device of claim 1, wherein the first locator orifice is a window that allows for the viewing of blood flow as the indication of blood flow.

9. The device of claim 1, wherein the first locator orifice is a gauge.

10. The device of claim 1, further comprising:
    an arteriotomy locator insertable through the sheath;
    wherein the arteriotomy locator includes an arteriotomy locator orifice disposed on the arteriotomy locator is in a position aligned with one of the first detection orifice or the second detection orifice when the arteriotomy locator is fully inserted into the sheath.

11. A method of positioning a vascular closure device comprising the steps of:
- inserting a distal end of a sheath through an existing tract to a blood vessel wall, a sealing device being insertable through the sheath;
- advancing the sheath through the blood vessel wall until blood flows into a first detection orifice of the sheath and blood flow is detected at a first locator orifice in the sheath;
- retracting the sheath until the blood flow ceases without completely withdrawing the sheath from the blood vessel and determining that the orifice is positioned adjacent an edge of the wall while the tip of the sheath is positioned within the blood vessel;
- wherein advancing the sheath forward further comprises stopping the forward advancement if blood flow is detected at a second locator orifice disposed in the sheath, wherein the second locator orifice is in fluid communication with a second detection orifice disposed further from the distal end of the sheath than the first orifice.

12. The method of claim 11, further comprising an arteriotomy locator wherein the arteriotomy locator is inserted through the sheath over a guidewire positioned in the blood vessel.

13. The method of claim 11, further comprising positioning a arteriotomy locator within the sheath as the sheath is inserted.

14. The method of claim 11, further comprising:
- passing an anchor member through the sheath;
- retracting the sheath from the blood vessel; and
- sealing a puncture in the blood vessel caused by the sheath with the anchor.

15. A method of using a vascular wound closure device for a vascular closure procedure, comprising:
- inserting a distal end of a sheath into an artery until blood flows into a first detection orifice and blood flow is detected at a first locator orifice in the sheath, the blood flow indicating that the first detection orifice has entered the artery;
- advancing the sheath a predetermined distance into the artery; and
- stopping advancement when blood flows into a second detection orifice of the sheath and blood flow is detected at a second locator orifice in the sheath, the second detection orifice being located proximal of the first detection orifice;
- wherein the sheath provides an access point for a sealing device into the artery.

16. A vascular wound closure device comprising:
- a sheath for penetrating an artery, the sheath having a distal end and a proximal end and providing an access point for a sealing device into the artery;
- a first detection orifice disposed on the sheath;
- a second detection orifice disposed on the sheath further from the distal end that then first detection orifice;
- a first indicator in fluid communication with the first detection orifice via a first fluid passageway, the first indicator disposed in the sheath proximate the proximal end, wherein the first indicator indicates when the first detection orifice is exposed to blood flow; and
- a second indicator in fluid communication with the second detection orifice via a second fluid passageway, the second indicator disposed in the sheath proximate the proximal end, wherein the second indicator indicates when the second detection orifice is exposed to blood flow.

17. The device of claim 16, wherein the first fluid passageway is a first lumen disposed within the sheath interconnecting first indicator with the first detection orifice.

18. The device of claim 17, wherein the second fluid passageway is a second lumen disposed within the sheath interconnecting second indicator with the second detection orifice.

19. The device of claim 16, wherein the first fluid passageway is formed from an gap between an internal portion of the sheath and a arteriotomy locator passed through the sheath.

* * * * *

UNITED STATES PATENT AND TRADEMARK OFFICE
CERTIFICATE OF CORRECTION

PATENT NO. : 7,850,654 B2  Page 1 of 1
APPLICATION NO. : 10/422614
DATED : December 14, 2010
INVENTOR(S) : Belhe et al.

It is certified that error appears in the above-identified patent and that said Letters Patent is hereby corrected as shown below:

SPECIFICATION

| Column | Line | PTO | Should Read |
| --- | --- | --- | --- |
| 4 | 7 | "steps of scaling a" | -- steps of sealing a -- |

Signed and Sealed this
Fifteenth Day of February, 2011

David J. Kappos
*Director of the United States Patent and Trademark Office*